United States Patent [19]
Neelakantan

[11] Patent Number: 5,872,087
[45] Date of Patent: Feb. 16, 1999

[54] HERBAL DRY SHAMPOO COMPOSITION

[75] Inventor: Kameswaran Neelakantan, T. Nagar Chennai, India

[73] Assignee: GEM Energy Industry Limited, Chennai, India

[21] Appl. No.: 984,251

[22] Filed: Dec. 3, 1997

[30] Foreign Application Priority Data

Jun. 20, 1997 [IN] India ............... 1351/MAS/97

[51] Int. Cl.⁶ ............... A61K 7/07; A61K 7/075; C11D 3/382; C11D 3/48

[52] U.S. Cl. ............... 510/119; 510/120; 510/438; 514/783; 424/70.1; 424/74; 424/195.1

[58] Field of Search .................. 510/438, 120, 510/119; 514/861, 783; 424/70.1, 74, 195.1

[56] References Cited

U.S. PATENT DOCUMENTS

| | | | |
|---|---|---|---|
| 4,581,230 | 4/1986 | Grollier et al. | 424/74 |
| 4,767,618 | 8/1988 | Grollier et al. | 424/74 |
| 5,578,312 | 11/1996 | Parrinello | 424/401 |

*Primary Examiner*—Ardith Hertzog
*Assistant Examiner*—Gregory E. Webb
*Attorney, Agent, or Firm*—Ladas & Parry

[57] ABSTRACT

A herbal dry shampoo composition comprising from about 6–12% by weight of foaming accelerating agent, from about 6–12% by weight of pigment recreating agent, from about 6–12% by weight of foaming agent, from about 6–12% by weight of conditioning agent and from about 52–76% by weight of preservative and hair stimulating agent where said constituents are cleaned, dried and crushed to a mesh size of 200–300 sieve size and maintaining the pH at 6–9.

11 Claims, No Drawings

HERBAL DRY SHAMPOO COMPOSITION

The present invention relates to herbal dry shampoo composition which is applied to the hair in powdered form.

BACKGROUND OF THE INVENTION

Dry powder shampoos are known but have not been particularly popular largely because they are rather inefficient in removing sebum from the hair.

The existing shampoos that are available in the market are mainly made out of inorganic chemicals, and even some of the so-called herbal shampoos contain inorganic chemicals to retain liquid form, which are injurious to human skin. The inorganic chemicals in the shampoo give a sheen or layer on the scalp of the skull between the hair roots which can lead to dandruff.

In some of the available dry shampoos, starch is used as the active powder, which tends to remain attached to the hair and is not readily removed. In some other shampoos it has been found that the dry shampoos can be formulated with other powders such as activated carbon and alumina. Even such shampoos are not desirable because they are not biodegradable and are difficult to remove form the hair.

It is therefore an object of the present invention to provide an efficient, non-toxic, biodegradable dry herbal powder shampoo composition.

It is another object of the present invention to provide a herbal dry shampoo composition having a longer shelf life.

The dry herbal shampoo of this invention has a shelf life of three to four years after it is packed.

One of the important objects of the present invention lies in the fact that the present invention is 100% herbal and no synthetic chemicals are used even for preservation. Constituents of the present composition act as preservatives.

SUMMARY OF THE INVENTION

The present herbal dry shampoo compositions of this invention comprise a mixture of herbs.

DETAILED DESCRIPTION OF THE INVENTION

The present invention relates to a herbal dry shampoo composition comprising:
  from about 6–12% by weight of a foaming accelerating agent,
  from about 6–12% by weight of a pigment recreating agent,
  from about 6–12% by weight of a foaming agent,
  from about 6–12% by weight of a conditioning agent and
  from about 52–76% by weight of preservative and hair stimulating agent.

A preferred embodiment of the invention is a composition of:
  from about 6–12% by weight of COCOA NUCIFERA
  from about 6–12% by weight of HIBISCUS ROSA SINESIS
  from about 6–12% by weight of SAPINDUS TRIFOLIATUS
  from about 6–12% by weight of TRIGONELLA FOENUM GRAECEUM
  from about 52–76% by weight of BASSIA MALABARICA

BASSIA MALABARICA

One of the major constituents in the present composition, it is a herb extracted from the genus Aisandra from the family Sapotaceae, large deciduous trees. The bark is dark reddish brown or dull black in color; leaves are long obveate-oblong or elliptic, pinkish white in color clustered at the end of branches having flowers of white or pale yellow color. The crushed and pulverzed leaves are used in the composition of this invention. They are used as a hair growth stimulant in the present shampoo composition and also act as preservative. The crushed and pulverized leaves are used in this composition. The present composition comprises 52–76% by weight of the leaves of Bassia malabarica.

COCOA NUCIFERA

A herb extracted from the genus Cocos of family Palmae. A tall and stately growing plant bearing a crown of large pinnate leaves. It contains potash and caprylic acid. It is used as foaming accelerating agent in the present composition and it is very useful for hair growth. The subject composition comprises 6–12% by weight of the kernal of Cocoa nucifera.

HIBISCUS ROSA SINESIS

Belongs to the genus Hibiscus from the family Malvaceae, a woody, glabrous, showy shrub having bright green leaves, flowers are solitary, axillary, bell-shaped, large, 4–6 inches in diameter with pistil and stamens projecting from the center, many contain seeds. The flowers of the plant are used in this composition. The constituents of the flowers stimulate the growth and color of the hair. It is used to recreate pigmentation to the hair. In the subject composition the flowers of the herb are used in the ratio of 6–12% by weight.

SAPINDUS TRIFOLIATUS

A herb from the genus Sapindus from the family Sapindaceae. A medium sized deciduous tree having shiny grey bark covered with rough, deciduous scales, having abruptly pinnate leaves and white colored flowers, seeds are pea-sized enclosed in blackish, smooth, hard endocarp. The leaves and seeds of the plant grows in a large form like a tree and the fruits are grown in bunches and clusters. When the fruits are dried they will have a color of dark reddish brown. The seeds inside are black in color. The fruit contains about 11.5% of saponin besides glucose and pectin and it also contains some white fat. The leaves and seeds of the plant are used for the composition of this invention. They are dried and converted to powders and used. They are used as a foaming agent in the present shampoo composition. The present composition comprises 6–12% by weight of the leaves and the seeds of Sapindus trifloliatus.

TRIGONELLA FOENUM GRAECEUM

A herb from the genus Trigonella from the family Leguminosae is an aromatic plant having pinnate, tri-foliate leaves and yellowish colored flowers. The seeds are greenish brown in color, oblong with a deep groove across one corner giving the seeds a hooked appearance. The seeds are dried and pulverized to form a powder which is used as a component of the shampoo. The powder contains albumin, choline and trigonelline. It contains substances rich in phosphates, lecithin and neucleo-albumin. It contains considerable quantities of iron in an organic form which enables it to be readily absorbed. It is used as a conditioner for the hair. In the present composition the seeds of the herb are added in the ratio of 6–12% by weight.

The present invention relates to a process for preparing a herbal dry shampoo composition comprising:

from about 6–12% by weight of foaming accelerating agent, from about 6–12% by weight of pigment recreating agent, from about 6–12% by weight of foaming agent, from about 6–12% by weight of conditioning agent and from about 52–76% by weight of preservative and hair stimulating agent.

To prepare this composition the constituents are cleaned, dried and crushed to a mesh size of 200–300 sieve size and the pH of the composition is 6–9.

All the above mentioned constituents of the present composition are plucked and processed and the process for preparing the composition comprises the steps of:

Cleaning of the constituents: The constituents are cleaned by conventional methods to remove all the superfluous dust and other foreign particles.

Drying of the constituents: The constituents are dried at ambient temperatures. It is preferred that they be dried in an open atmosphere.

Crushing of the constituents in the pulverizer: All the constituents are meshed in a pulverizer to a mesh size of 200–300. At the time of crushing the constituents, the pH is maintained at 7. A pH adjusting agent such as sodium bicarbonate is used to adjust the pH.

Packing of the said mixture: After the desired mesh size is achieved the powdered mixture is removed from the pulverizer and packed.

The mixture so prepared has a shelf life of three to four years, because of the presence of a herbal preservative such as *Bassia malabarica*. The present invention is illustrated by the examples given below which should not be construed to limit the scope of the invention.

EXAMPLE-I

The following herbs are used in the preparation of a herbal dry shampoo composition comprising:

from about 9–12% by weight of COCOA NUCIFERA from about 9–12% by weight of HIBISCUS ROSA SINESIS from about 9–12% by weight of SAPINDUS TRIFOLIATUS from about 9–12% by weight of TRIGONELLA FOENUM GRAECEUM and from about 52–64% by weight of BASSIA MALABARICA The constituents are cleaned, dried at ambient temperatures and crushed to a mesh size of 175–275 sieve size maintaining the pH at 6–9, and finally packed.

EXAMPLE-II

The following herbs are used in the preparation of a herbal dry shampoo composition comprising:

from about 6–9% by weight of COCOA NUCIFERA from about 6–9% by weight of HIBISCUS ROSA SINESIS from about 6–9% by weight of SAPINDUS TRIFOLIATUS from about 6–9% by weight of TRIGONELLA FOENUM GRAECEUM and from about 64–76% by weight of BASSIA MALABARICA The constituents are cleaned, dried at ambient temperatures and crushed to the mesh size of 150–350 sieve size maintaining the pH at 6–9, and finally packed.

The present invention is advantageous because the present herbal shampoo composition is a 100% herbal product where no synthetic or artificial chemicals are added. In the present invention no artificial preservatives is used to increase the life of the product as the natural herb of the present composition itself acts as a preservative. The present composition has a shelf life of more than three years without any contamination or fungal growth. The present composition is very economical one as all the essential ingredients are natural and are found in abundance. All the important constituents of the present invention are non-toxic according to the intended use.

We claim:

1. A herbal dry shampoo composition comprising:

from about 6–12% by weight of a foaming accelerating agent, from about 6–12% by weight of a pigment recreating agent, from about 6–12% by weight of a foaming agent, from about 6–12% by weight of a conditioning agent and from about 52–76% by weight of *Bassia malabarica*.

2. A herbal dry shampoo composition as claimed in claim 1 wherein *Cocoa nucifera* is the foaming accelerating agent.

3. A herbal dry shampoo composition as claimed in claim 1 wherein *Hibiscus rosa sinesis* is the pigment recreating agent.

4. A herbal dry shampoo composition as claimed in claim 1 wherein *Sapindus trifloiatus* is the foaming agent.

5. A herbal dry shampoo composition as claimed in claim 1 wherein *Trigonella foenum graceum* is the conditioner.

6. A herbal dry shampoo composition according to claim 1 having a shelf life of more than three years.

7. A herbal dry shampoo composition according to claim 1 having a pH of from 6 to 9.

8. A dry herbal shampoo composition comprising:

from about 6–12% by weight of COCOA NUCIFERA, from about 6–12% by weight of HIBISCUS ROSA SINESIS, from about 6–12% by weight of SAPINDUS TRIFOLIATUS, from about 6–12% by weight of TRIGONELLA FOENUM GRAECEUM and from about 52–76% by weight of BASSIA MALABARICA.

9. A process for the preparation of herbal dry shampoo composition of claim 8 comprising the steps of a) cleaning leaves of *Bassia malabarica*, kernals of *Cocoa nucifera*, flowers of *Hibiscus rosa sinesis*, leaves and seeds of *Sapindus trioliatus* and seeds of *Trigonella foenum graecum*, b) drying the cleaned constituents of step a) at ambient temperatures, and c) crushing and mixing the constituents.

10. A herbal dry shampoo composition as claimed in claim 8 wherein mesh size of the composition is 200–300 sieve size.

11. A herbal dry shampoo composition as claimed in claim 8 wherein pH is maintained at 7 at the time of crushing of the constituents of the composition.

* * * * *